(12) United States Patent
Trenhaile

(10) Patent No.: US 11,707,353 B2
(45) Date of Patent: Jul. 25, 2023

(54) SYSTEMS FOR KNOTLESS TISSUE REPAIR

(71) Applicant: Smith & Nephew, Inc., Memphis, TN (US)

(72) Inventor: Scott William Trenhaile, Belvidere, IL (US)

(73) Assignee: SMITH & NEPHEW, INC., Memphis, TN (US)

(*) Notice: Subject to any disclaimer, the term of this patent is extended or adjusted under 35 U.S.C. 154(b) by 296 days.

(21) Appl. No.: 16/652,438

(22) PCT Filed: Oct. 16, 2018

(86) PCT No.: PCT/US2018/056093
§ 371 (c)(1),
(2) Date: Mar. 31, 2020

(87) PCT Pub. No.: WO2019/079306
PCT Pub. Date: Apr. 25, 2019

(65) Prior Publication Data
US 2020/0253715 A1 Aug. 13, 2020

Related U.S. Application Data

(60) Provisional application No. 62/574,273, filed on Oct. 19, 2017.

(51) Int. Cl.
*A61F 2/08* (2006.01)
*A61B 17/04* (2006.01)
*A61B 17/06* (2006.01)

(52) U.S. Cl.
CPC ........ *A61F 2/0811* (2013.01); *A61B 17/0401* (2013.01); *A61B 17/06166* (2013.01);
(Continued)

(58) Field of Classification Search
CPC ........... A61B 17/0401; A61B 17/06166; A61F 2002/0852
See application file for complete search history.

(56) References Cited

U.S. PATENT DOCUMENTS 3,918,455 A * 11/1975 Coplan ............ A61B 17/06004
223/102
2007/0191849 A1* 8/2007 ElAttrache ......... A61B 17/0401
606/326

(Continued)

*Primary Examiner* — Alexander J Orkin
(74) *Attorney, Agent, or Firm* — Burns & Levinson LLP; Joseph M. Maraia; Marlo Schepper Grolnic

(57) ABSTRACT

Systems and methods for knotless tissue repair employ a first suture construct routed through a tissue in a first inverted mattress stitch, including a loop portion and two free limbs. The loop portion of the first suture construct so routed is positioned adjacent to a superior surface of the tissue and the free limbs of the first suture construct so routed extend through an inferior surface of the tissue. A second suture construct, separate from the first suture construct, is inserted within the loop portion of the first suture construct such that two free limbs of the second suture construct extend from the loop portion of the first suture construct. The second suture construct comprises a plurality of braided filaments and possesses a substantially rectangular cross-sectional profile, and does not include a suture core surrounded by the braided filaments.

21 Claims, 15 Drawing Sheets

(52) U.S. Cl.
CPC .............. *A61F 2002/0852* (2013.01); *A61F 2002/0894* (2013.01)

(56) References Cited

U.S. PATENT DOCUMENTS

| | | | | |
|---|---|---|---|---|
| 2007/0219558 | A1* | 9/2007 | Deutsch | A61B 17/0401 606/326 |
| 2012/0059417 | A1* | 3/2012 | Norton | A61B 17/0401 606/232 |
| 2012/0130422 | A1* | 5/2012 | Hootstein | A61B 17/0401 606/228 |
| 2012/0265219 | A1* | 10/2012 | Rushdy | A61B 17/0401 606/139 |
| 2013/0096612 | A1* | 4/2013 | Zajac | A61B 17/0469 606/232 |
| 2013/0296893 | A1* | 11/2013 | Dean | A61B 17/06166 606/228 |
| 2013/0296936 | A1* | 11/2013 | Burkhart | A61B 17/0401 606/232 |
| 2013/0345749 | A1* | 12/2013 | Sullivan | A61B 17/0469 606/232 |
| 2015/0216522 | A1* | 8/2015 | Ticker | A61B 17/0401 606/232 |
| 2017/0095324 | A1* | 4/2017 | Adams | A61B 17/0401 |
| 2018/0000480 | A1* | 1/2018 | Dumanian | A61B 17/06066 |

* cited by examiner

SYSTEMS FOR KNOTLESS TISSUE REPAIR

CROSS-REFERENCE TO RELATED APPLICATIONS

This application is the U.S. national phase entry under 35 U.S.C. § of International Application No. PCT/US2018/056093, filed Oct. 16, 2018, entitled SYSTEMS FOR KNOTLESS TISSUE REPAIR, which in turn claims priority to and benefit of U.S. Provisional Application No. 62/574,273, filed Oct. 19, 2017, the contents of which are incorporated herein by reference in their entirety for all purposes.

BACKGROUND

The shoulder joint, also referred to as the glenohumeral joint, is the joint located between the glenoid cavity (a part of the scapula) and the head of the humerus (the upper arm bone). The glenoid cavity is shallow, covering only about a third of the head humeral head. As a result, the glenoid cavity provides relatively little bony constraint upon motion of the humerus. Instead, a group of muscles and tendons attached to the humeral head, collectively referred to as the rotator cuff, function to stabilize the glenohumeral joint and assist in performing arm motions such as lifting and rotation.

The rotator cuff may become torn from overuse or injury, with at least a portion of the tendons of the rotator cuff detached from the humeral head. Left untreated, the rotator cuff tear may enlarge over time and, in extreme cases, the rotator cuff tendons may become completely severed from attachment with the humerus. A torn rotator cuff compromises stabilization of the glenohumeral joint and increases the likelihood of glenohumeral joint dislocation, where the humerus is forced from its normal anatomical position with respect to the glenoid socket. Thus, while not life threatening, rotator cuff injuries can cause pain and/or restricted movement (even immobilization, in extreme cases) of the glenohumeral joint, impacting a patient's lifestyle.

A variety of techniques have been developed for rotator cuff repair. For example, transosseous equivalent repair has become popular for medium to large rotator cuff repairs. This repair technique involves tying medial row knots in at least one strand of suture from two or more medial row anchors. Subsequently, loose limbs of suture extending from the knot are spanned over to the lateral row to provide a broad area of compression over the rotator cuff. The sutures are formed into knots to secure their position with respect to the anchors. This technique, however, is problematic when conducted arthroscopically. Notably, given the relatively small amount of space in which arthroscopic procedures are formed, tying knots under these conditions is technically challenging. As a result, the likelihood that a surgeon commits an error in tying knots arthroscopically may be increased, as compared to non-arthroscopic repair techniques. Such errors may, in turn, create a potential point of failure and/or delay during such operations.

An alternative knotless technique, referred to as Speedbridge™ (Arthrex, Inc., Naples, Fla., USA), has been developed for use using the FiberTape® (Arthrex, Inc., Naples, Fla., USA) product. FiberTape® is a composite suture composed of a multi-strand core of ultra-high molecular weight polyethylene (UHMWPE) with a braided jacket of polyester and UHMWPE. The FiberTape® is passed through the rotator cuff at the medial row location and spanned down to a second set of knotless anchors laterally. No medial row knot is tied, as the FiberTape® product cannot be tied arthroscopically. However, the use of FiberTape® can be problematic in that it may have abrasive qualities.

When complete rotator cuff repair is not technically achievable, another method of repair, known as a superior capsular reconstruction (SCR), may be employed as an alternative treatment. SCR places a tissue graft into the subacromial space spanning the humeral head and the glenoid neck. However, current solutions for arthroscopic SCR are difficult to perform due to intensive suture management and complicated steps. Such complexity makes the procedures less reproducible because of the number of steps involved and the possible pitfalls along the way.

Accordingly, there is a continued need for improved surgical techniques for arthroscopic, knotless rotator cuff repair.

SUMMARY

Embodiments of the present disclosure are directed to improved systems and methods for arthroscopic joint repair. Accordingly, certain embodiments of the disclosed methods are directed to systems and methods for arthroscopic rotator cuff repair. It has become recognized that increased suture contact area and distribution of pressure upon the rotator cuff repair surgery may aid post-operative healing. Accordingly, embodiments of the disclosed repair advantageously may employ one or more braided suture constructs that provide greater contact area and pressure distribution with soft tissue, than comparable, alternative suture systems.

Further embodiments of the systems and methods for knotless tissue repair of this disclosure may include one or more of the following, in any suitable combination.

In one example, the method of this disclosure includes routing a first suture construct through a tissue in a first inverted mattress stitch, including a loop portion and two free limbs. The loop portion of the first suture construct is positioned adjacent to a superior surface of the tissue and the free limbs of the first suture construct extend through an inferior surface of the tissue. The method also includes inserting a second suture construct, separate from the first suture construct, within the loop portion of the first suture construct such that two free limbs of the second suture construct extend from the loop portion of the first suture construct. The second suture construct is made from a plurality of braided filaments and possesses a substantially rectangular cross-sectional profile, and does not include a suture core surrounded by the braided filaments. The method also includes securing the free limbs of the first suture construct to a humeral head at a selected medial location with respect to the tissue without forming a knot with the free limbs of the first suture construct, and approximating the tissue down to the humeral head at the selected medial location. Finally, the method includes extending the free limbs of the second suture construct to one or more selected lateral locations with respect to the tissue, whereby at least a portion of the tissue is urged laterally, and securing the free limbs of the second suture construct to the humeral head at the one or more selected lateral locations without forming a knot with the free limbs of the second suture construct. The portion of the second suture construct extending between the selected medial location and the one or more selected lateral locations contacts the superior surface of the tissue.

In further examples of the method, securing the free limbs of the first suture construct to the humeral head includes inserting at least a portion of each of the free limbs of the first suture construct into a first knotless suture anchor and implanting the first knotless suture anchor into the humeral head at the selected medial location. In further examples, securing the free limbs of the second suture construct to the humeral head includes inserting at least a portion of the free limbs of the second suture construct into a second knotless suture anchor and implanting the second knotless suture anchor into the humeral head at the selected lateral location. In further examples, routing the first suture construct through the tissue includes routing a first pair of suture constructs through the tissue, each one of the first pair of suture constructs having a loop portion. Inserting the second suture construct within the loop portion of the first suture construct includes inserting a second pair of suture constructs within the loop portions of the first pair of suture constructs, respectively. In examples, the tissue is a rotator cuff or a graft.

In further examples, the method includes routing a third suture construct through the tissue in a second inverted mattress stitch, including a loop portion and two free limbs. The loop portion of the third suture construct so routed is positioned adjacent to the superior surface of the tissue and the free limbs of the first suture construct so routed extend through the inferior surface of the tissue. The method also includes inserting a fourth suture construct, separate from the third suture construct, within the loop portion of the third suture construct such that two free limbs of the fourth suture construct extend from the loop portion of the third suture construct. The method further includes securing the free limbs of the third suture construct to a glenoid at a selected glenoid location with respect to the tissue without forming a knot with the free limbs of the third suture construct, and approximating the tissue down to the glenoid at the selected glenoid location. Finally, the method includes extending the free limbs of the fourth suture construct to the one or more selected lateral locations with respect to the tissue, whereby at least a portion of the tissue is urged laterally, and securing the free limbs of the fourth suture construct to the humeral head at the one or more selected lateral locations without forming a knot with the free limbs of the fourth suture construct. The portion of the fourth suture construct extending between the selected glenoid location and the one or more selected lateral locations contacts the superior surface of the tissue.

In yet further examples, securing the free limbs the third suture construct to the glenoid includes inserting at least a portion of each of the free limbs of the third suture construct into the third knotless suture anchor, and implanting the third knotless suture anchor and free limbs of the third suture construct into the glenoid at the selected glenoid location. Securing the free limbs of the fourth suture construct to the humeral head includes inserting at least a portion of the free limbs of the fourth suture construct into the second knotless suture anchor. Routing the third suture construct through the tissue includes routing a third pair of suture constructs through the tissue, each one of the third pair of suture constructs having a loop portion. Inserting the fourth suture construct within the loop portion of the third suture construct includes inserting a fourth pair of suture constructs within the loop portions of the third pair of suture constructs, respectively. In examples, the method further includes routing a first lateral suture and a second lateral suture through opposing corners of the tissue such that two free limbs of each of the first and second lateral sutures extend from the superior surface of the tissue. In examples, the method further includes securing the free limbs of the first lateral suture and the second lateral suture to the humeral head at the one or more selected lateral locations with respect to the tissue after said routing without forming a knot with the free limbs of the first lateral suture and the second lateral suture. In examples, securing the free limbs of the first lateral suture and the second lateral suture to the humeral head includes inserting at least a portion of the free limbs of the first lateral suture and the second lateral suture into the second knotless suture anchor.

Examples of a suture/tissue construct for use in a knotless tissue repair of this disclosure include a tissue having a superior surface and an inferior surface. The construct also includes a first suture construct routed through the tissue at a selected medical location with respect to the tissue in a first inverted mattress stitch, including a loop portion and two free limbs. The loop portion of the first suture construct so routed is positioned adjacent to the superior surface of the tissue and the free limbs of the first suture construct so routed extend through the inferior surface of the tissue. The construct also includes a second suture construct, separate from the first suture construct, inserted within the loop portion of the first suture construct such that two free limbs of the second suture construct extend from the loop portion of the first suture construct. The second suture construct is made of a plurality of braided filaments and possesses a substantially rectangular cross-sectional profile, and does not include a suture core surrounded by the braided filaments. In examples, the first suture construct includes a first pair of suture constructs, each one of the first pair of suture constructs having a loop portion. In examples, the second suture construct includes a second pair of suture constructs, each one of the second pair of suture constructs inserted within the loop portions of the first pair of suture constructs, respectively. In examples, the tissue is a rotator cuff or a graft.

In further examples, the suture/tissue construct includes a third suture construct routed through the tissue at a selected glenoid location with respect to the tissue in a second inverted mattress stitch, including a loop portion and two free limbs. The loop portion of the third suture construct so routed is positioned adjacent to the superior surface of the tissue and the free limbs of the first suture construct so routed extend through the inferior surface of the tissue. The construct also includes a fourth suture construct, separate from the third suture construct, inserted within the loop portion of the third suture construct such that two free limbs of the fourth suture construct extend from the loop portion of the third suture construct. In examples, the third suture construct includes a third pair of suture constructs, each one of the third pair of suture constructs having a loop portion. In examples, the fourth suture construct includes a fourth pair of suture constructs, each one of the fourth pair of suture constructs inserted within the loop portions of the third pair of suture constructs, respectively. In further examples, the construct includes a first lateral suture and a second lateral suture routed through opposing corners of the tissue such that two free limbs of each of the first and second lateral sutures extend from the superior surface of the tissue. In examples, construct is preassembled prior to introduction of the construct into a joint space.

When used in embodiments of the disclosed rotator cuff repair method, the braided suture construct may distribute forces to underlying soft tissue more uniformly, and over a greater area, than alternative suture systems, which is expected to lead to improved clinical outcomes following rotator cuff repair. It is also anticipated that the braided suture construct system may also lower the pressure applied upon the soft tissue, reducing vascular constriction, and reducing the likelihood of tissue tearing when routed through, and applying force upon, soft tissue. Advantageously, each of these characteristics may further support healing.

BRIEF DESCRIPTION OF THE DRAWINGS

The foregoing and other objects, features and advantages will be apparent from the following more particular description of the embodiments, as illustrated in the accompanying drawings in which like reference characters refer to the same parts throughout the different views. The drawings are not necessarily to scale, emphasis instead being placed upon illustrating the principles of the embodiments.

DETAILED DESCRIPTION

Figure 1:
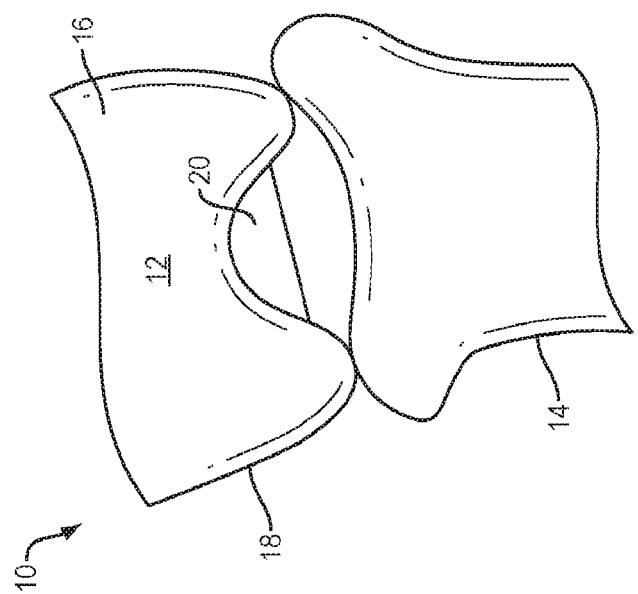
FIG. 1 is a schematic illustration of a torn rotator cuff.

In the description that follows, like components have been given the same reference numerals, regardless of whether they are shown in different examples. To illustrate an example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

The terms "comprise," "include," and/or plural forms of each are open ended and include the listed parts and can include additional parts that are not listed. "And/or" is open ended and includes one or more of the listed parts and combinations of the listed parts.

A schematic illustration of a damaged glenohumeral joint 10, including a rotator cuff 12 and a head of the humerus (i.e., humeral head 14) is shown in FIG. 1. A superior surface 16 of the rotator cuff 12 is visible, while an opposing, inferior surface 18 is not visible. The joint damage is manifested as partial tear 20 in the rotator cuff 12, where a portion of the tendons at the ends of the rotator cuff 12 are severed from the humeral head 14. While the tear 20 of FIG. 1 is illustrated as a partial tear, embodiments of the disclosure may also be employed for repair of full rotator cuff tears, as necessary.

With reference to FIGS. 2A-2E, embodiments of a method for repairing a damaged rotator cuff 12, such as that of FIG. 1, will now be discussed. However, it may be understood that the disclosed embodiments may be employed in other types of joint repair involving soft tissue to bone fixation without limit. Embodiments may include, but are not limited to, Achilles tendon repair, patellar tendon repair, and hip abductor repair.

Figure 2A:
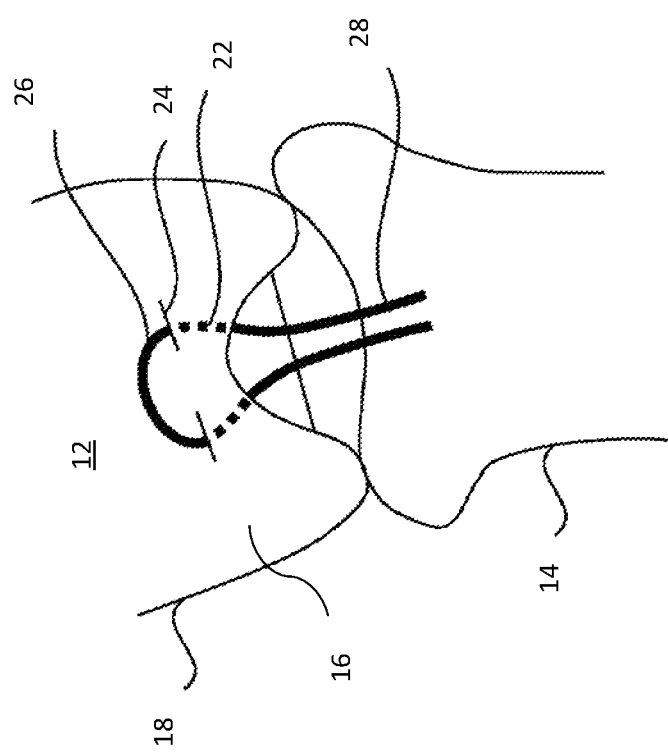
FIGS. 2A-E are schematic illustrations of an embodiment of a knotless rotator cuff repair technique employing a braided suture construct.
Figure 2B:
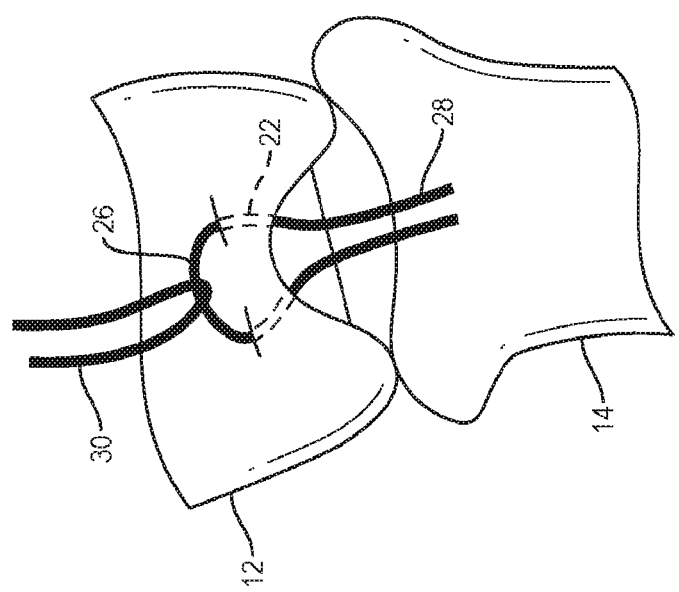

As illustrated in FIG. 2A, embodiments of the method include routing a first suture construct 22 through the rotator cuff 12. In an embodiment, a plurality of portals 24 may be formed through the rotator cuff 12, either before or during such routing, extending between the superior surface 16 and inferior surface 18 of the rotator cuff 12. The positions of the portals 24 may be suitable for subsequent placement at a desired medial location of the humeral head 14, as further described below. In an embodiment, the first suture construct 22 may be routed through the rotator cuff 12 in a "mattress stitch," as known in the art. In certain embodiments, the mattress stitch may be a horizontally inverted mattress stitch, although other mattress stitches, such as a vertically inverted mattress stitches, are possible. After routing through the rotator cuff 12, a portion of the first suture construct 22 forms a loop 26 positioned adjacent to the superior surface 16 of the rotator cuff 12. Free limbs 28 of the first suture construct 22 further extend from the loop 26 and through the inferior surface 18 of the rotator cuff 12. With reference to FIG. 2B, embodiments of the method may further include inserting a second suture construct 30 within the loop 26 of the first suture construct 22. Non-limiting examples of inserting the second suture construct 30 within the loop 26 of the first suture construct 22 may include tying, looping or weaving the second suture construct 30 within the loop 26 of the first suture construct 22. After this insertion, two free limbs 30 of the second suture construct 30 extend from the loop 26 of the first suture construct 22.

The first suture construct 22 and the second suture construct 30 may be formed from non-absorbable, sterile surgical sutures, although very slow resorption type sutures could also be used. In an embodiment, the first suture construct 22 may consist essentially of a #2 suture, as known in the art. In a further embodiment, the second suture construct 30 may comprise a braided suture construct, woven from a plurality of filaments. In further embodiments, the second suture construct 30 may consist essentially of the braided suture construct, without a separate suture core. The filaments may be formed from a polymer (e.g., ultra-high molecular weight polyethylene). In certain embodiments, this braided suture architecture exhibits a generally flat (e.g., rectangular) cross-sectional profile. In further embodiments, the braided suture architecture may possess a width within the range between about 1.85 to about 2.5 mm. In an embodiment, the braided suture architecture may possess a width of about 2 mm. In additional embodiments, the braided suture architecture may possess a height within the range between about 0.15 to about 0.45 mm. In an embodiment, the braided suture architecture may possess a height of about 0.3 mm. In certain embodiments, the braided suture construct may satisfy the U.S. Pharmacopeial Convention (USP) average knot-pull tensile strength requirements for nonabsorbable #2 suture as given in the USP Monograph USP 37-NF32:2014 "Nonabsorbable Surgical Suture." In certain embodiments, the average knot-pull tensile strength of the braided suture construct may fall within the range between about 88 N to about 156 N. Non-limiting examples of the braided suture construct may include, but are not limited to, ULTRATAPE (Smith & Nephew, Inc., Memphis, Tenn., USA). In additional embodiments, both the first suture construct 22 and the second suture construct 30 may be formed from this braided suture construct.

Figure 2C:
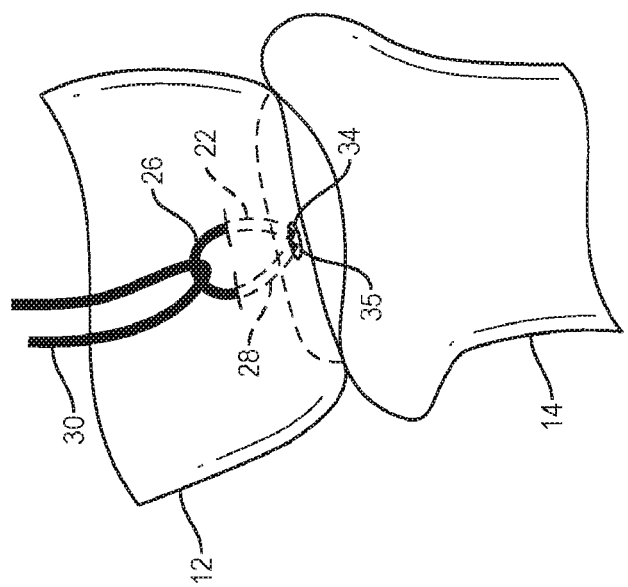

With reference to FIG. 2C, embodiments of the method may further include securing the free limbs 28 of the first suture construct 22 to the humeral head 14. In an embodiment, the free limbs 28 of the first suture construct 22 are secured to the humeral head 14 after inserting the second suture construct 30 within the loop 26 of the first suture construct 22. In an alternative embodiment, the free limbs 28 of the first suture construct 22 are secured to the humeral head 14 before inserting the second suture construct 30 within the loop 26 of the first suture construct 22 by engaging the second suture construct 30 on the top of the first suture construct 22 before securing the first suture construct 22 to the rotator cuff 12. For example, securing the first suture construct 22 to the humeral head 14 may include selecting a desired medial location 35 of the humeral head 14. At least a portion of the free limbs 28 of the first suture construct 22 may be inserted into a medial row anchor 34. The medial row anchor 34 may be subsequently implanted into the desired medial location 35. The medial row anchor 34 may be a knotless suture anchor, many examples of which are known in the art. Accordingly, in certain embodiments, securing the first suture construct 22 to the humeral head 14 may not include forming a knot with the free limbs 28 of the first suture construct 22. Rather, the free limbs 28 of the first suture construct 22 may be frictionally secured to the medial row anchor 34 by pressure exerted upon the free limbs 28. Such pressure may be exerted by the medial row anchor 34, the surrounding bone, or combinations thereof.

Still referring to FIG. 2C, embodiments of the method may further include approximating the rotator cuff 12 down to the humeral head 14 at the selected medial location 35. In an embodiment, the rotator cuff 12 is approximated to the humeral head 14 by pulling on the free limbs 28 either before or after the insertion of the free limbs 28 into the medial row anchor 34 (or both before and after microadjustments of rotator cuff 12 reduction). Once the rotator cuff 12 is reduced to the humeral head 14 and the medial row anchor 34 is inserted into the humeral head 14, the medial row tendon (not shown) is secured with a locking mechanism. In another example, such approximation may be performed after securing the first suture construct 22 to the humeral head 14. In alternative embodiments, such approximation may be performed before securing the first suture construct 22 to the humeral head 14. Advantageously, this provides a "knot-like" point of fixation at the medial location 35.

Figure 2D:
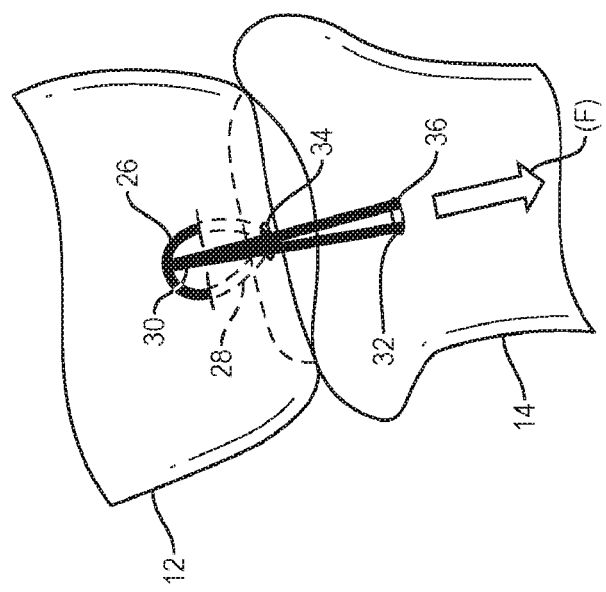
Figure 2E:
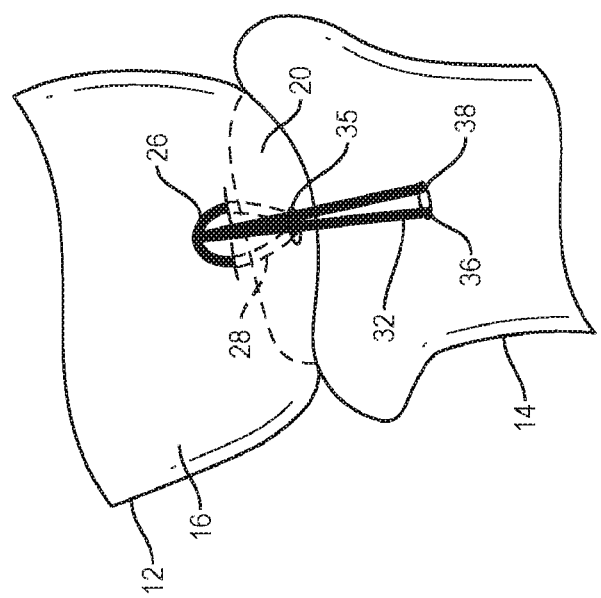

With reference to FIG. 2D, the two free limbs 32 of the second suture construct 30 are extended towards one or more selected lateral locations 36. So extended, the free limbs 32 of the second suture construct 30 exert a reduction force (F) on the rotator cuff 12 and urge at least a portion of the rotator cuff 12 laterally. As illustrated in FIG. 2E, in certain embodiments, both of the free limbs 32 of the second suture construct 30 may be extended towards the same lateral location 36. Once positioned, the second suture construct 30 may be secured to the humeral head 14. For example, a portion of the free limbs 32 of the second suture construct 30 may be inserted into a lateral row anchor 38. In embodiments, the lateral row anchor 38 may be a knotless suture anchor. Accordingly, in certain embodiments, securing the second suture construct 30 to the humeral head 14 may not include forming a knot with the free limbs 32 of the second suture construct 30. Rather, the free limbs 32 of the second suture construct 30 may be frictionally secured to the lateral row anchor 38 by pressure exerted upon the free limbs 32. Such pressure may be exerted by the lateral row anchor 38, the surrounding bone, or combinations thereof. The lateral row anchor 38 may be subsequently implanted into the desired lateral location 36. Once the second suture construct 30 is secured at the one or more selected lateral locations 36, a portion of the second suture construct 30 extends between the selected medial location 35 and lateral location 36, overlying and contacting the superior surface 16 of the rotator cuff 12. The pressure applied by the second suture construct 30 upon the rotator cuff 12 urges the rotator cuff 12 into contact with the humeral head 14, facilitating repair of the tear 20.

Figure 3A:
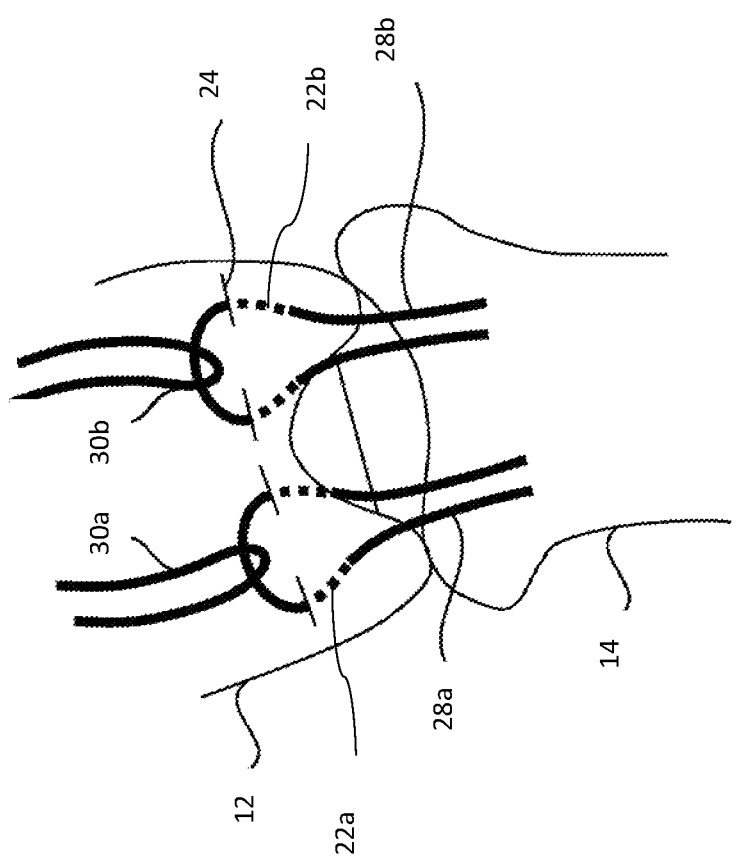
FIGS. 3A-C are schematic illustrations of another embodiment of a knotless rotator cuff repair technique employing a braided suture construct.
Figure 3B:
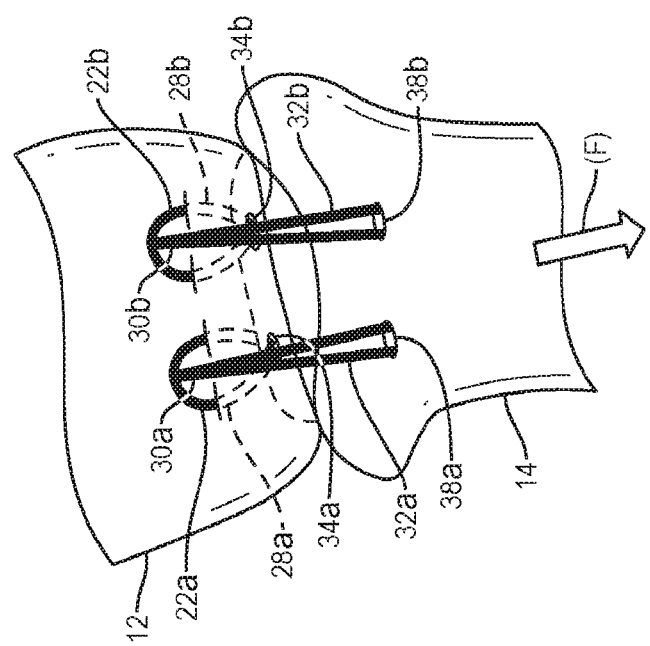
Figure 3C:
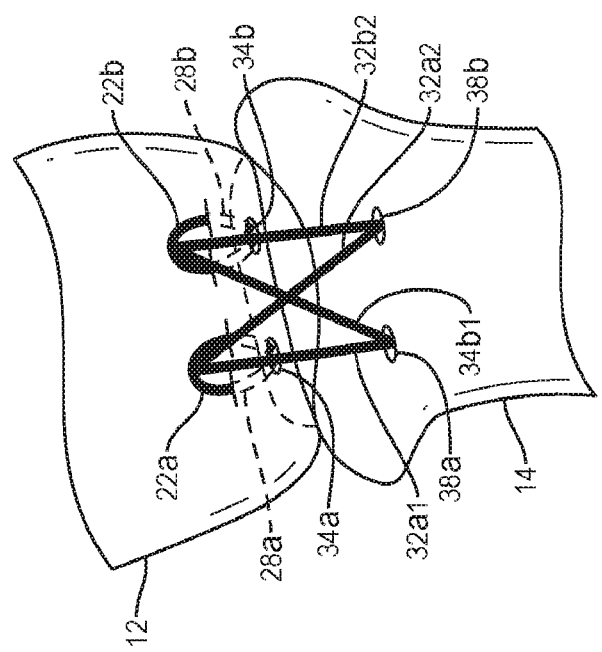

In alternative embodiments of the method, more than one first suture construct 22 and second suture construct 30 may be employed for rotator cuff repair. For example, as illustrated in FIG. 3A, two pairs of first suture constructs 22a,b and second suture constructs 30a,b may be employed. In alternative embodiments, the number of first and second suture construct pairs may be increased, without limit. Each pair of first suture constructs 22a,b and second suture constructs 30a,b may be secured to the humeral head 14 in the same manner as discussed above with respect to FIGS. 2A-2E. FIG. 3B shows a closed system with the free limbs 28a of first suture construct 22a routed to a first medial row anchor 34a, and the free limbs 28b of first suture construct 22b routed to a second medial row anchor 34b. The free limbs 32a of second suture construct 30a are routed to a first lateral row anchor 38a, and the free limbs 32b of second suture construct 30b are routed to a second lateral row anchor 38b. FIG. 3C shows a suture bridge-like interconnection in which the free limb 32a1 of second suture construct 30a and the free limb 32b1 of second suture construct 30b are routed to the first lateral row anchor 38a, and the free limb 32a2 of second suture construct 30a and the free limb 32b2 of second suture construct 30b are routed to the second lateral row anchor 38b.

Turning now to FIGS. 4A-F, an example of a method of SCR for repairing a glenohumeral joint will now be discussed. The methods of SCR of this disclosure are similar to the methods described above with respect to FIGS. 1-3C, except as described below. It may be also be understood that the disclosed embodiments may be employed in other types of joint repair involving soft tissue to bone fixation without limit.

Figure 4A:
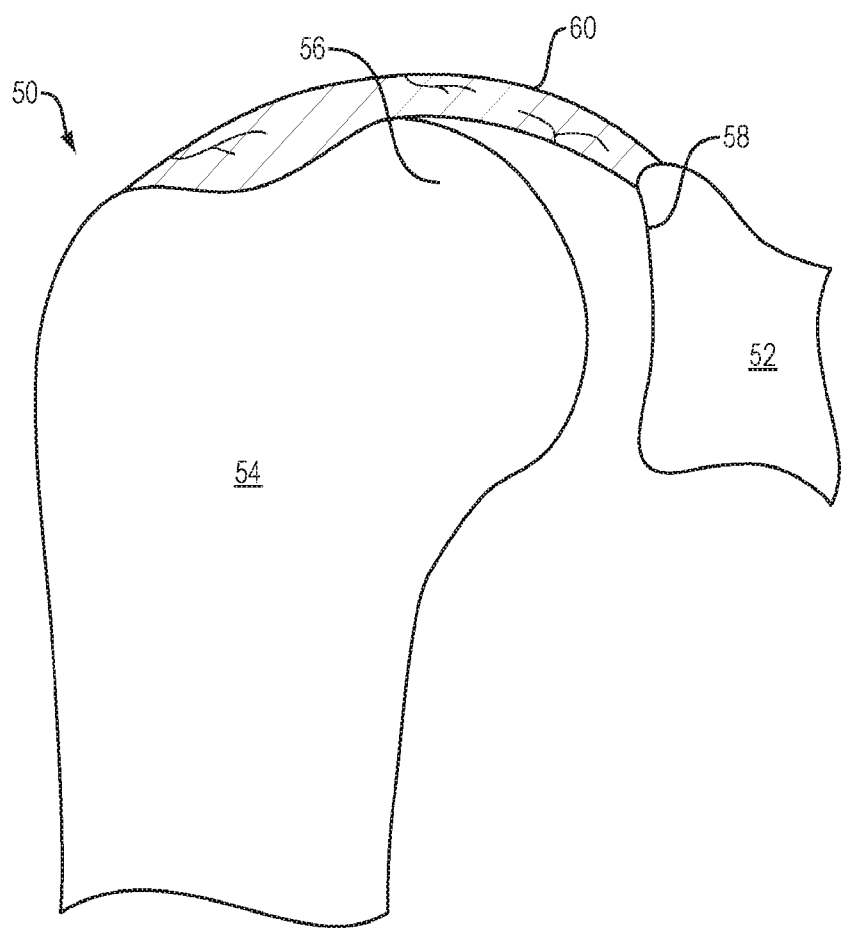
FIGS. 4A-F are schematic illustrations of an embodiment of a knotless superior capsular reconstruction technique employing a braided suture construct.
Figure 4B:
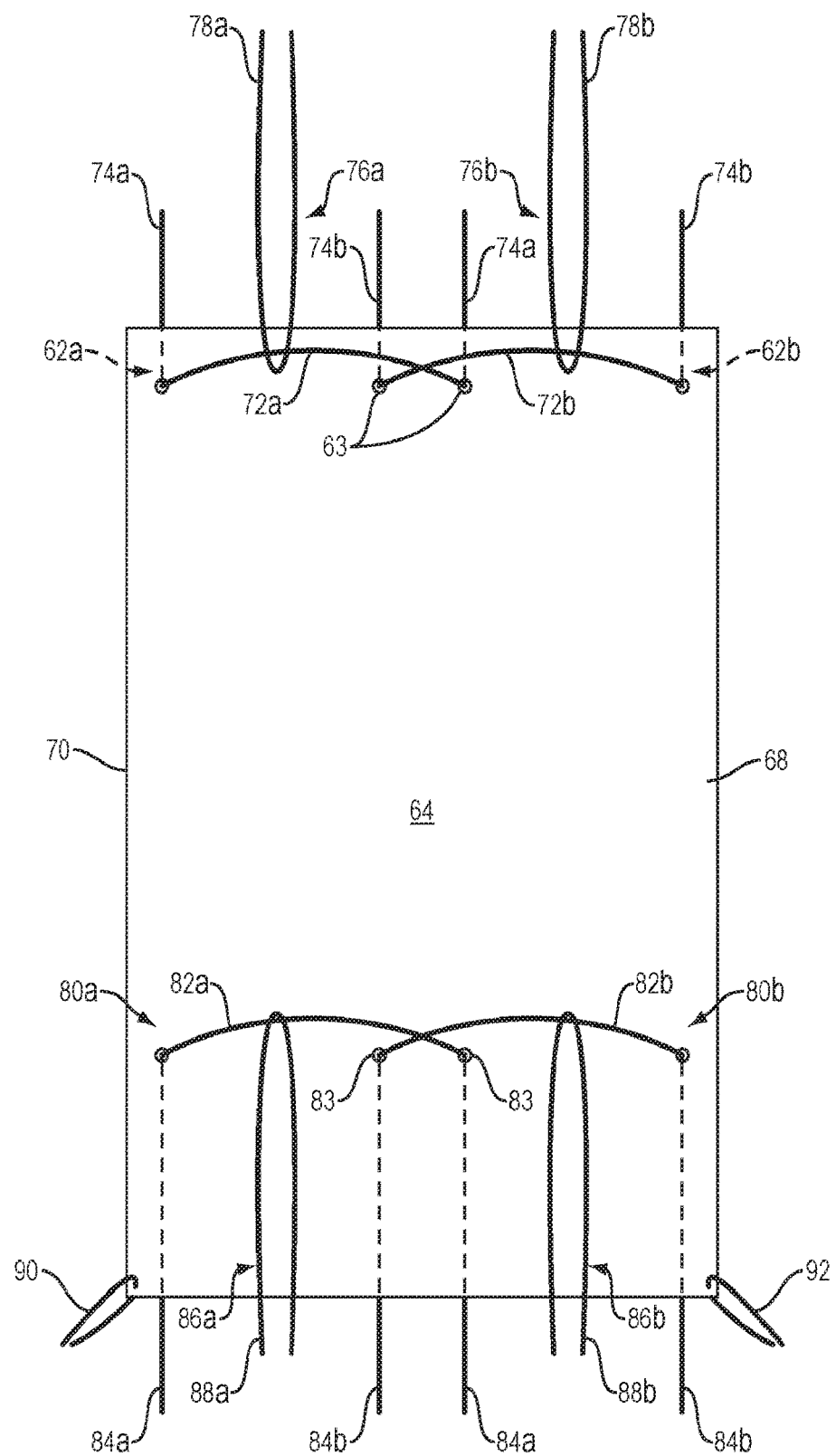
Figure 4C:
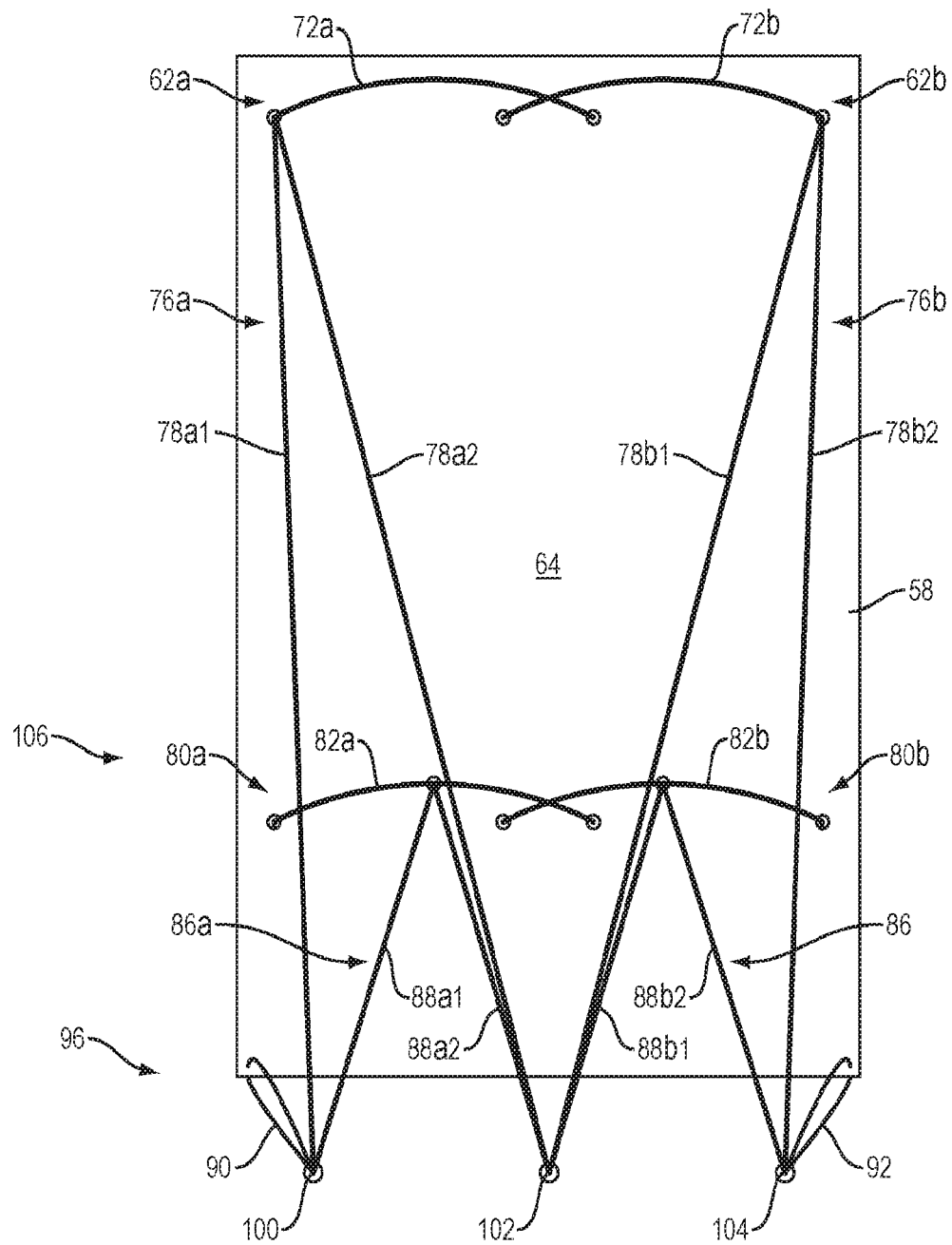
Figure 4D:
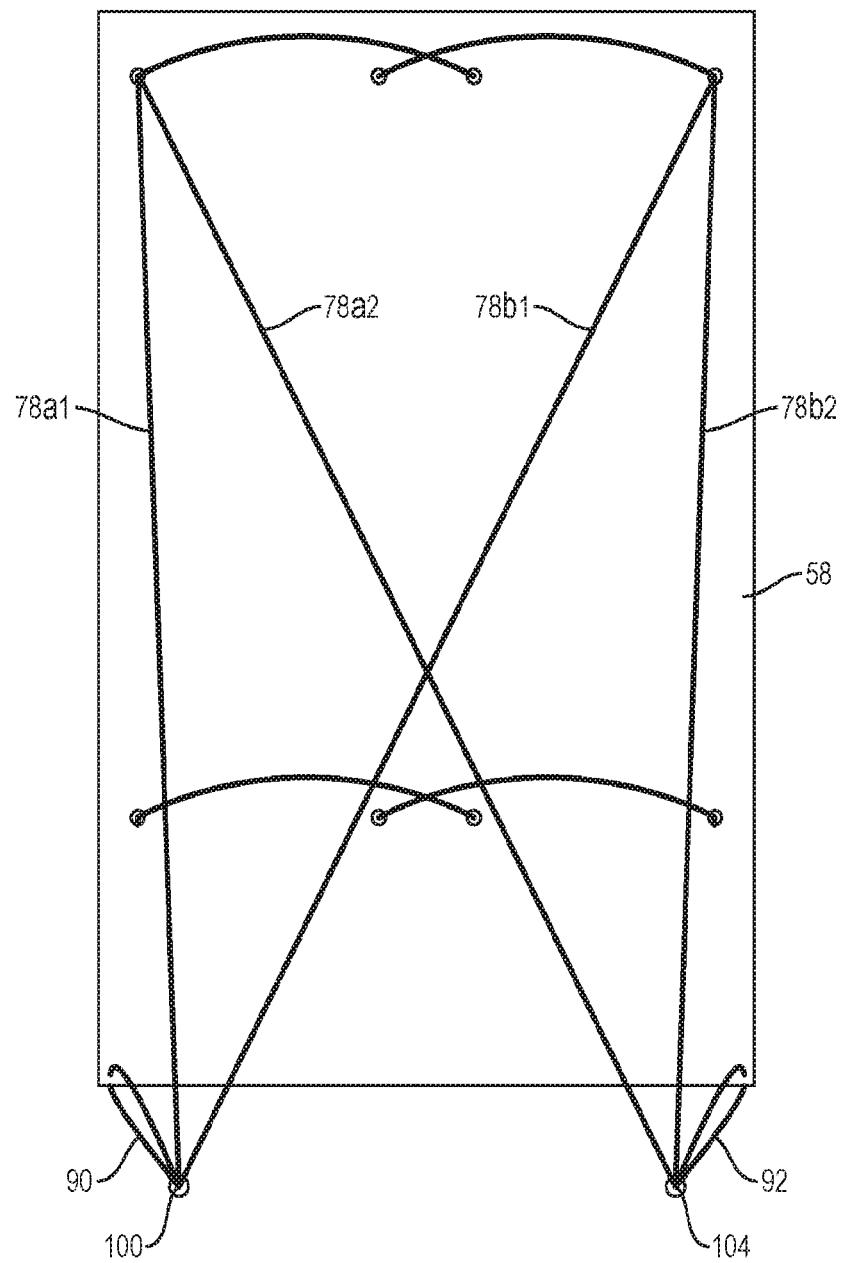
Figure 4E:
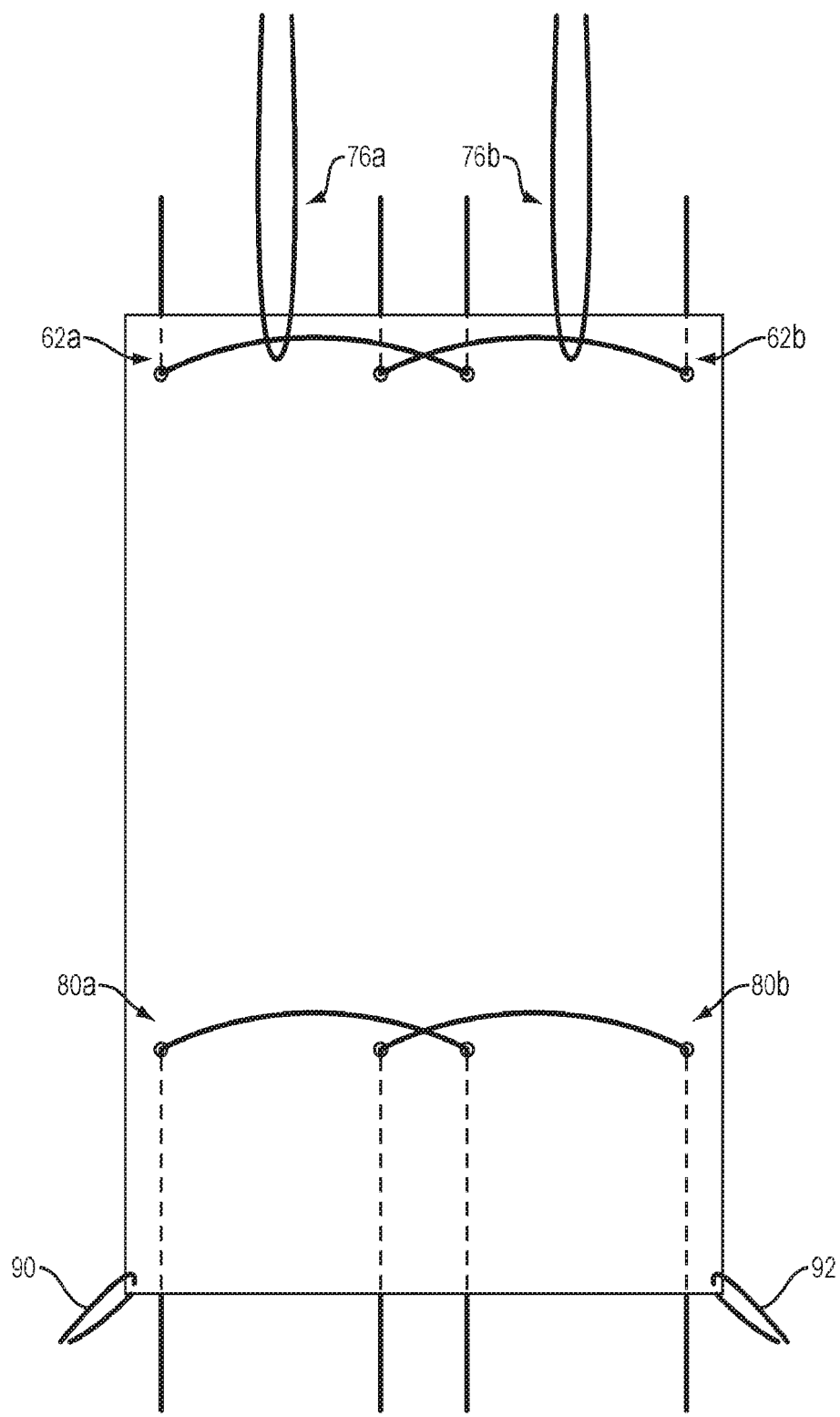
Figure 4F:
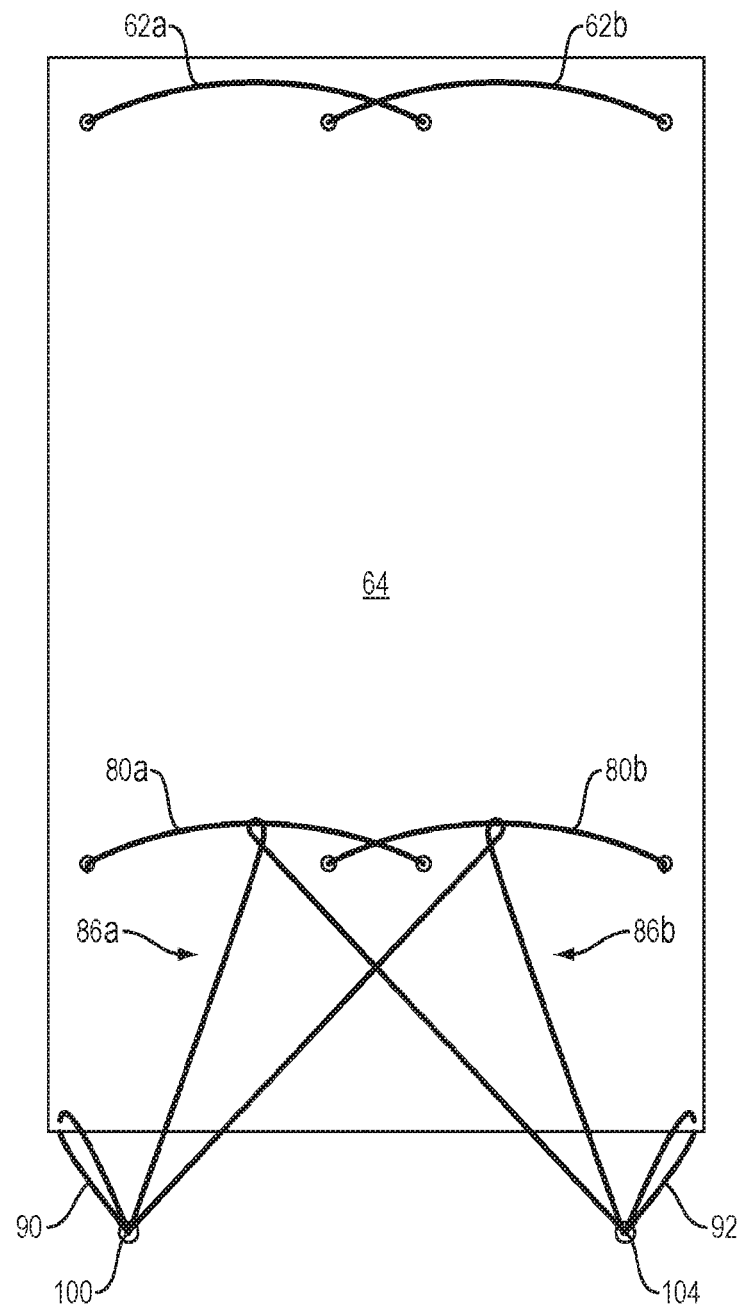

With reference to FIG. 4A, a glenohumeral joint 50 of the human musculoskeletal system is illustrated. The joint 50 includes multiple bones, including a scapula 52 and a humerus 54, which may articulate relative to one another. For example, the joint 50 includes a ball and socket joint formed between a head 56 of the humerus 54 and a glenoid 58, which is a cup-like recession of the scapula 52 configured to receive the humeral head 56. A capsule 60 generally covers the joint 50 and is surrounded and reinforced by various muscles, tendons and ligaments that are responsible for keeping the adjoining bones of the joint 50 together. The joint 50 may become unstable if there is significant disruption of the articulating bones (e.g., the humerus 54 and the glenoid 58), the capsule 60, or other surrounding muscles, tendons and/or ligaments. For example, the joint 50 could become unstable in response to an irreparable rotator cuff tear. In FIGS. 4B-D, the bones of the joint 50 are omitted from the figures for ease of illustration.

With reference to FIG. 4B, embodiments of the method of SCR include routing a first pair of suture constructs 62a,b through a graft 64, such as a dermal graft. In an embodiment, a plurality of portals 63 may be formed through the graft 64, either before or during such routing, extending between the superior surface 68 and the inferior surface 70 of the graft 64. The positions of the portals 63 may be suitable for subsequent placement at a desired glenoid location of the glenoid 58 (FIG. 4A), as further described below. In an embodiment, the first pair of suture constructs 62a,b may be routed through the graft 64 in a mattress stitch. After routing through the graft 64, a portion of the first pair of suture constructs 62a,b forms a first pair of loops 72a,b positioned adjacent to the superior surface 68 of the graft 64. Free limbs 74a,b of the first pair of suture constructs 62a,b further extend from the loops 72a,b and through the inferior surface 70 of the graft 64. In the example of FIG. 4B, the mattress stitches may be routed through the graft 64 such that the loops 72a,b overlap to further aid in compression of the graft 64. In other embodiments (not shown) the mattress stitches may be routed through the graft 64 such that the loops 72a,b share a common portal 63 near the center of the graft 64. Embodiments of the method may further include inserting a second pair of suture constructs 76a,b within the respective loops 72a,b of the first pair of suture construct 62a,b. After this insertion, two free limbs 78a,b of the second pair of suture construct 76a,b extend from the respective loops 72a,b of the first pair of suture constructs 62a,b.

Still referring to FIG. 4B, embodiments of the method may further include routing a third pair of suture constructs 80a,b through the graft 64. In an embodiment, a plurality of portals 83 may be formed through the graft 64, either before or during such routing, extending between the superior surface 68 and the inferior surface 70 of the graft 64. The positions of the portals 83 may be suitable for subsequent placement at a desired medial location of the humeral head 56 (FIG. 4A), as further described below. In an embodiment, the third pair of suture constructs 80a,b may be routed through the graft 64 in a mattress stitch. After routing through the graft 64, a portion of the third pair of suture constructs 80a,b forms a second pair of loops 82a,b positioned adjacent to the superior surface 68 of the graft 64. Free limbs 84a,b of the third pair of suture constructs 80a,b further extend from the loops 82a,b and through the inferior surface 70 of the graft 64. In the example of FIG. 4B, the mattress stitches may be routed through the graft 64 such that the loops 82a,b overlap to further aid in compression of the graft 64. In other embodiments (not shown) the mattress stitches may be routed through the graft 64 such that the loops 82a,b share a common portal 83 near the center of the graft 64. Embodiments of the method may further include inserting a fourth pair of suture constructs 86a,b within the respective loops 82a,b of the third pair of suture constructs 80a,b. After this insertion, two free limbs 88a,b of the fourth pair of suture constructs 86a,b extend from the respective loops 82a,b of the third pair of suture constructs 80a,b. In further embodiments, two lateral sutures 90, 92 can optionally be attached to opposing corners of the graft 64. The lateral sutures 90, 92 may include individual suture strands, multiple suture strands, suture tape or any other suture-like product. The lateral sutures 90, 92 are attached to the graft 64 such that two suture limbs extend from the superior surface 68 graft 64. For example, a "luggage tag" stitch may be used, as known in the art. Advantageously, it is contemplated that all sutures shown in FIG. 4B could be passed through the graft 64 prior to introduction of the graft 64 into the endoscopic subacromial space, including the lateral sutures 90, 92. This is especially beneficial since passing the lateral sutures 90, 92 in the graft 64 is difficult given the thickness of the graft 64.

With reference to FIG. 4C, embodiments of the method may further include securing the free limbs (not shown) of the pair of first suture constructs 62a,b to the glenoid 58. For example, securing the first pair of suture constructs 62a,b to the glenoid 58 may include selecting a desired glenoid location of the glenoid 58. At least a portion of the free limbs of the first pair of suture constructs 62a,b may be inserted into at least one glenoid row anchor (not shown). The glenoid row anchor may be subsequently implanted into the desired glenoid location. The glenoid row anchor may be a knotless suture anchor. Accordingly, in certain embodiments, securing the first pair of suture constructs 62a,b to the glenoid 58 may not include forming a knot with the free limbs of the first pair of suture constructs 62a,b. In embodiments, the method may further include approximating the graft 64 down to the glenoid 58 at the selected glenoid location. In an embodiment, the graft 64 is approximated to the glenoid 58 by pulling on the free limbs of the first pair of suture constructs 62a,b either before or after the insertion of the free limbs into the glenoid row anchor (or both before and after micro-adjustments of graft reduction). The free limbs 78a1,a2,b1,b2 of the second pair of suture constructs 76a,b are then extended towards one or more selected lateral locations 96 on the humerus 54. Once positioned, the second pair of suture constructs 76a,b may be secured to the humeral head 56. For example, a portion of the free limbs 78a1,a2,b1,b2 of the second pair of suture constructs 76a,b may be inserted into three lateral row anchors 100, 102, 104. However, it is contemplated by this disclosure that more or fewer than three lateral row anchors may be used. In embodiments, the lateral row anchors 100, 102, 104 may be a knotless suture anchors. Accordingly, in certain embodiments, securing the second pair of suture constructs 76a,b to the humerus 54 may not include forming a knot with the free limbs 78a,b of the second pair of suture constructs 76a,b. The lateral row anchors 100, 102, 104 may be subsequently implanted into the desired lateral location 96. Once the second pair of suture constructs 76a,b is secured at the one or more selected lateral locations 96, a portion of the second pair of suture constructs 76a,b extends between the glenoid 54 and the lateral location 96 of the humerus, overlying and contacting the superior surface 58 of the graft 64.

Still in reference to FIG. 4C, embodiments of the method may further include securing the free limbs (not shown) of the third pair of suture constructs 80a,b to the humerus 54. For example, securing the third pair of suture constructs 80a,b to the humerus may include selecting a desired medial location 106 of the humerus 54. At least a portion of the free limbs of the third pair of suture constructs 80a,b may be inserted into at least one medial row anchor (not shown). The medial row anchor may be subsequently implanted into the desired medial location 106 of the humerus 54. In embodiments, the medial row anchor may be a knotless suture anchor. Accordingly, in certain embodiments, securing the third pair of suture constructs 80a,b to the humerus 54 may not include forming a knot with the free limbs of the third pair of suture constructs 80a,b. In embodiments, the method may further include approximating the graft 64 down to the humerus 54 at the selected medial location 106 by pulling on the free limbs of the third pair of suture constructs 80a,b either before or after the insertion of the free limbs into the medial row anchor (or both before and after micro-adjustments of graft reduction). The free limbs 88a1,a2,b1,b2 of the fourth pair of suture constructs 86a,b are extended towards the one or more selected lateral locations 96 on the humerus 54. Once positioned, the fourth pair of suture constructs 86a,b may be secured to the humeral head 56. For example, a portion of the free limbs 88a1,a2,b1,b2 of the fourth pair of suture constructs 86a,b may be inserted into at least one of the lateral row anchors 100, 102, 104. However, it is contemplated by this disclosure that the portion of the free limbs 88a,b may be secured to one or more additional lateral anchors, not shown. Once the fourth pair of suture constructs 86a,b is secured at the one or more selected lateral locations 96, a portion of the fourth pair of suture constructs 86a,b extends between the medial location 106 and the lateral location 96 of the humerus 54, overlying and contacting the superior surface 58 of the graft 64.

Notably, in FIG. 4C, both of the free limbs 78a2 and 78b1 of the second pair of suture constructs 76a,b are shown as inserted into the same lateral row anchor 102, while free limb 78a1 is inserted into lateral row anchor 100 and free limb 78*b*2 is inserted into the lateral row anchor 104. Additionally, both of the free limbs 88*a*2 and 88*b*1 of the fourth pair of suture constructs 86*a,b* are inserted into lateral row anchor 102, while free limb 88*a*1 is inserted into lateral row anchor 100 and free limb 88*b*2 is inserted into the lateral row anchor 104. Finally, lateral row suture 90 is inserted into lateral row anchor 100, while lateral row suture 92 is inserted into lateral row anchor 104. However, other suture/anchor configurations are contemplated by this disclosure without limit. For example, in FIG. 4D, only two lateral row anchors 100, 104 are used. Free limbs 78*a*1 and 78*b*1, as well as lateral suture 90, are attached to lateral row anchor 100, while free limbs 78*a*2 and 78*b*2, as well as lateral suture 92, are attached to lateral row anchor 104.

It will be appreciated that many variations of the methods described above with regard to FIGS. 4A-C are contemplated by this disclosure. In one non-limiting example, shown in FIG. 4E, only the first pair of suture constructs 62*a,b*, the second pair of suture constructs 76*a,b*, the third pair of suture constructs 80*a,b*, and the lateral sutures 90, 92 are used to secure the graft 64 using three lateral row anchors (not shown). In another non-limiting example, shown in FIG. 4F, the second pair of suture constructs 76*a,b* could be omitted, and the fourth pair of suture constructs 86*a,b* used instead, along with two lateral row anchors 100, 104. However, it is contemplated that other combinations of suture constructs, lateral sutures, and lateral anchors, could be used to secure the graft 64.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

What is claimed is:

1. A method of tissue repair, comprising:
routing a pair of first suture constructs through a tissue, each one of the pair of first suture constructs including a loop portion and two free limbs, wherein the loop portions of the pair of first suture constructs so routed are positioned adjacent to a superior surface of the tissue and each free limb of the pair of first suture constructs so routed extends through a separate hole in the tissue to an inferior surface of the tissue, and wherein the loop portions of the pair of first suture constructs and each of the separate holes in the tissue are adjacent a first end of the tissue;
inserting a pair of second suture constructs, separate from the pair of first suture constructs, within the loop portions of a respective one of the pair of first suture constructs such that first and second free limbs of the pair of second suture constructs extend from the loop portions of the pair of first suture constructs;
securing the free limbs of the pair of first suture constructs to a first bone at a selected medial location with respect to the tissue after said routing without forming a knot with the free limbs of the pair of first suture constructs;
approximating the tissue down to the first bone at the selected medial location;
extending the first and second free limbs of the pair of second suture constructs toward a second end of the tissue opposite the first end without passing through the tissue, whereby at least a portion of the tissue is urged laterally; and
securing the first and second free limbs of the pair of second suture constructs to a second bone at one or more selected lateral locations without forming a knot with the first and second free limbs of the pair of second suture constructs;
wherein the portions of the pair of second suture constructs extending between the selected medial location and the one or more selected lateral locations contacts the superior surface of the tissue; and
wherein securing the first and second free limbs of the pair of second suture constructs to the second bone comprises:
inserting at least a portion of the first free limb of one of the pair of second suture constructs into a first knotless suture anchor;
inserting at least a portion of the second free limb of the one of the pair of second suture constructs into a second knotless suture anchor;
inserting at least a portion of the first free limb of another of the pair of second suture constructs into the second knotless suture anchor;
inserting at least a portion of the second free limb of the other of the pair of second suture constructs into a third knotless suture anchor; and
implanting the first, second, and third knotless suture anchor into the second bone at the one of more selected lateral locations, a position of the second knotless suture anchor being between the first and the third knotless suture anchors.

2. The method of claim 1, wherein securing the free limbs of the pair of first suture constructs to the first bone comprises:
inserting at least a portion of each of the free limbs of the pair of first suture constructs into a fourth knotless suture anchor; and
implanting the fourth knotless suture anchor into the first bone at the selected medial location.

3. The method of claim 1, wherein the loop portion of one of the pair of first suture constructs overlaps the loop portion of another one of said pair of first suture constructs.

4. The method of claim 1, wherein the tissue is a rotator cuff.

5. The method of claim 1, wherein the tissue is a graft.

6. The method of claim 1, further comprising:
routing a third suture construct through the tissue, the third suture construct including a loop portion and two free limbs, wherein the loop portion of the third suture construct so routed is positioned adjacent to the superior surface of the tissue and each free limb of the third suture construct so routed extends through a separate hole in the tissue to the inferior surface of the tissue, and wherein the loop portion of the third suture construct and each of the separate holes in the tissue are adjacent the second end of the tissue;
inserting a fourth suture construct, separate from the third suture construct, within the loop portion of the third suture construct such that first and second free limbs of the fourth suture construct extend from the loop portion of the third suture construct;
securing the free limbs of the third suture construct to the second bone at a selected intermediate location with respect to the tissue after said routing without forming a knot with the free limbs of the third suture construct;

approximating the tissue down to the second bone at the selected intermediate location;

extending the first and second free limbs of the fourth suture construct to the one or more selected lateral locations with respect to the tissue toward the second end of the tissue without passing through the tissue, whereby at least a portion of the tissue is urged laterally; and securing the first and second free limbs of the fourth suture construct to the second bone at the one or more selected lateral locations without forming a knot with the first and second free limbs of the fourth suture construct;

wherein the portion of the fourth suture construct extending between the selected intermediate location and the one or more selected lateral locations contacts the superior surface of the tissue.

7. The method of claim 6, wherein securing the free limbs of the third suture construct to the second bone comprises:

inserting at least a portion of each of the free limbs of the third suture construct into a fifth knotless suture anchor; and implanting the fifth knotless suture anchor into the second bone at the selected intermediate location.

8. The method of claim 6, wherein securing the first and second free limbs of the fourth suture construct to the second bone comprises inserting at least a portion of the first free limb of the fourth suture construct into the first knotless suture anchor.

9. The method of claim 6, wherein routing the third suture construct through the tissue comprises routing a third pair of suture constructs through the tissue, each suture construct of said third pair of suture constructs comprising a loop portion that overlaps the loop portion of the other suture construct of said third pair of suture constructs.

10. The method of claim 9, wherein inserting the fourth suture construct within the loop portion of the third suture construct comprises inserting a fourth pair of suture constructs within the loop portions of the third pair of suture constructs, respectively.

11. The method of claim 1, further comprising:

routing a first lateral suture and a second lateral suture through opposing corners of the tissue such that two free limbs of each of the first and second lateral sutures extend from the superior surface of the tissue; and securing the free limbs of the first lateral suture and the second lateral suture to the second bone at the one or more selected lateral locations with respect to the tissue after said routing without forming a knot with the free limbs of the first lateral suture and the second lateral suture.

12. The method of claim 11, wherein securing the free limbs of the first lateral suture and the second lateral suture to the second bone comprises inserting at least a portion of the free limbs of the first lateral suture into the first knotless suture anchor.

13. The method of claim 1, wherein the first bone is a glenoid.

14. The method of claim 1, wherein the second bone is a humeral head.

15. A suture/tissue graft construct for use in a knotless tissue repair, the suture/tissue construct comprising:

a tissue graft having a superior surface and an inferior surface;

a pair of first suture constructs routed through the tissue graft at a selected medical location with respect to the tissue graft, each one of the pair of first suture constructs including a loop portion and two free limbs, wherein the loop portions of the pair of first suture construct so routed are positioned adjacent to the superior surface of the tissue graft and each free limb of the pair of first suture construct so routed extends through a separate hole in the tissue graft to the inferior surface of the tissue graft, the loop portions of the pair of first suture constructs and each of the separate holes in the tissue graft being adjacent a first end of the tissue graft; and a pair of second suture constructs, separate from the pair of first suture construct, inserted within the loop portions of a respective on of the pair of first suture constructs such that first and second free limbs of the pair of second suture constructs extend from the loop portions of the pair of first suture constructs toward a second end of the tissue graft opposite the first end without passing through the tissue graft;

wherein at least a portion of the first free limb of one of the pair of second suture constructs is inserted into a first knotless suture anchor, at least a portion of the second free limb of the one of the pair of second suture constructs is inserted into a second knotless suture anchor, at least a portion of the first free limb of another of the pair of second suture constructs is inserted into the second knotless suture anchor, and at least a portion of the second free limb of the other of the pair of second suture constructs is inserted into a third knotless suture anchor.

16. The suture/tissue graft construct of claim 15, wherein the loop portion of one of the pair of first suture constructs overlaps the loop portion of another one of said pair of first suture constructs.

17. The suture/tissue graft construct of claim 15, further comprising:

a third suture construct routed through the tissue graft at a selected intermediate location with respect to the tissue graft, the third suture construct including a loop portion and two free limbs, wherein the loop portion of the third suture construct so routed is positioned adjacent to the superior surface of the tissue graft and each free limb of the third suture construct so routed extends through a separate hole in the tissue graft to the inferior surface of the tissue graft, and wherein the loop portion of the third suture construct and each of the separate holes in the tissue graft are adjacent the second end of the tissue graft; and a fourth suture construct, separate from the third suture construct, inserted within the loop portion of the third suture construct such that first and second free limbs of the fourth suture construct extend from the loop portion of the third suture construct toward the second end of the tissue graft without passing through the tissue graft.

18. The suture/tissue graft construct of claim 17, wherein the third suture construct comprises a third pair of suture constructs, each suture construct of said third pair of suture constructs comprising a loop portion that overlaps the loop portion of the other suture construct of said third pair of suture constructs.

19. The suture/tissue graft construct of claim 18, wherein the fourth suture construct comprises a fourth pair of suture constructs, each one of the fourth pair of suture constructs inserted within the loop portions of the third pair of suture constructs, respectively.

20. The suture/tissue graft construct of claim 15, further comprising:
 a first lateral suture and a second lateral suture routed through opposing corners of the tissue graft such that two free limbs of each of the first and second lateral sutures extend from the superior surface of the tissue graft.

21. The suture/tissue graft construct of claim 15 being preassembled prior to introduction of the construct into a joint space.

* * * * *